US 6,716,165 B1

(12) United States Patent
Flanders et al.

(10) Patent No.: US 6,716,165 B1
(45) Date of Patent: Apr. 6, 2004

(54) PATIENT TELEMETRY DEVICE AND LEADSET DESIGNS FOR PROVIDING ANTENNA DIVERSITY

(75) Inventors: Edward L. Flanders, Coto de Caza, CA (US); Scott J. Carter, Seal Beach, CA (US); Robert B. Kato, Lake Forest, CA (US)

(73) Assignee: GE Medical Systems Information Technologies, Inc., Milwaukee, WI (US)

( * ) Notice: Subject to any disclaimer, the term of this patent is extended or adjusted under 35 U.S.C. 154(b) by 495 days.

(21) Appl. No.: 09/854,169

(22) Filed: May 11, 2001

Related U.S. Application Data

(60) Provisional application No. 60/273,136, filed on Mar. 2, 2001.

(51) Int. Cl.$^7$ .................................................. A61B 5/00
(52) U.S. Cl. ...................... 600/301; 600/509; 600/372; 343/718; 128/903
(58) Field of Search ................................ 600/301, 509, 600/300, 372; 342/463; 343/718; 607/30, 31, 32, 33, 340, 60; 128/903, 904

(56) References Cited

U.S. PATENT DOCUMENTS

| 3,618,097 A | 11/1971 | McLeon, Jr. |
| 3,631,851 A | 1/1972 | Hesen |
| 3,919,644 A | 11/1975 | Smolka |
| 4,186,347 A | 1/1980 | Frosch et al. |
| 4,492,962 A | 1/1985 | Hansen |
| 4,539,710 A | 9/1985 | Dinsmore |
| 4,543,955 A | 10/1985 | Schroeppel |
| 4,741,341 A | 5/1988 | Marach |
| 5,231,990 A | 8/1993 | Gauglitz |
| 5,333,617 A | 8/1994 | Hafner |
| 6,526,310 B1 * | 6/1996 | Dondale ............... 600/509 |
| 5,579,001 A | 11/1996 | Dempsey et al. |
| 5,687,734 A | 11/1997 | Dempsey et al. |
| 5,694,940 A | 12/1997 | Unger et al. |
| 5,748,103 A | 5/1998 | Flach et al. |
| 5,767,791 A | 6/1998 | Stoop et al. |
| 5,944,659 A | 8/1999 | Flach et al. |
| 6,121,940 A | 9/2000 | Skahill et al. |
| 6,213,942 B1 * | 4/2001 | Flach et al. ............ 600/300 |
| 6,216,038 B1 | 4/2001 | Hartlaub et al. |
| 6,263,235 B1 | 7/2001 | Kaiser et al. |
| 6,272,379 B1 | 8/2001 | Fishell et al. |
| 6,438,407 B1 | 8/2002 | Ousdigian et al. |
| 6,529,164 B1 * | 3/2003 | Carter .................. 342/463 |
| 6,567,703 B1 | 5/2003 | Thompson et al. |
| 6,611,705 B2 * | 8/2003 | Hopman et al. ........ 600/509 |
| 6,636,761 B2 * | 10/2003 | Brodnick ............... 600/509 |
| 6,643,540 B2 * | 11/2003 | Yonce .................. 600/509 |
| 6,647,286 B1 * | 11/2003 | Katon et al. ........... 600/509 |

* cited by examiner

Primary Examiner—Henry Bennett
Assistant Examiner—Fadi H. Dahbour
(74) Attorney, Agent, or Firm—Foley & Lardner

(57) ABSTRACT

Various designs and features of an ambulatory transceiver and ECG lead set are disclosed for use in remote patient monitoring. One feature involves the use of unshielded, dual-conductor lead wires in which one conductor carries the patient's ECG signal and the other conductor provides an RF antenna element for the transceiver. The lead wires used in one embodiment provide improved flexibility, durability, and antenna performance over conventional lead sets with shielded wires. Another feature involves an antenna diversity scheme in which the transceiver switches between two or more ECG-lead antennas, each of which is formed from one or more ECG leads of the lead set. Another feature involves the use of a circuit within the transceiver to monitor, and dynamically compensate for changes in, the impedance of an ECG-lead antenna or a conductor thereof. Another feature is an improved circuit for protecting the transceiver from damage caused by defibrillation pulses.

58 Claims, 10 Drawing Sheets

| KEY | |
|---|---|
| RL | = RIGHT LEG |
| LA | = LEFT ARM |
| C | = CHEST |
| LL | = LEFT LEG |
| RA | = RIGHT ARM |

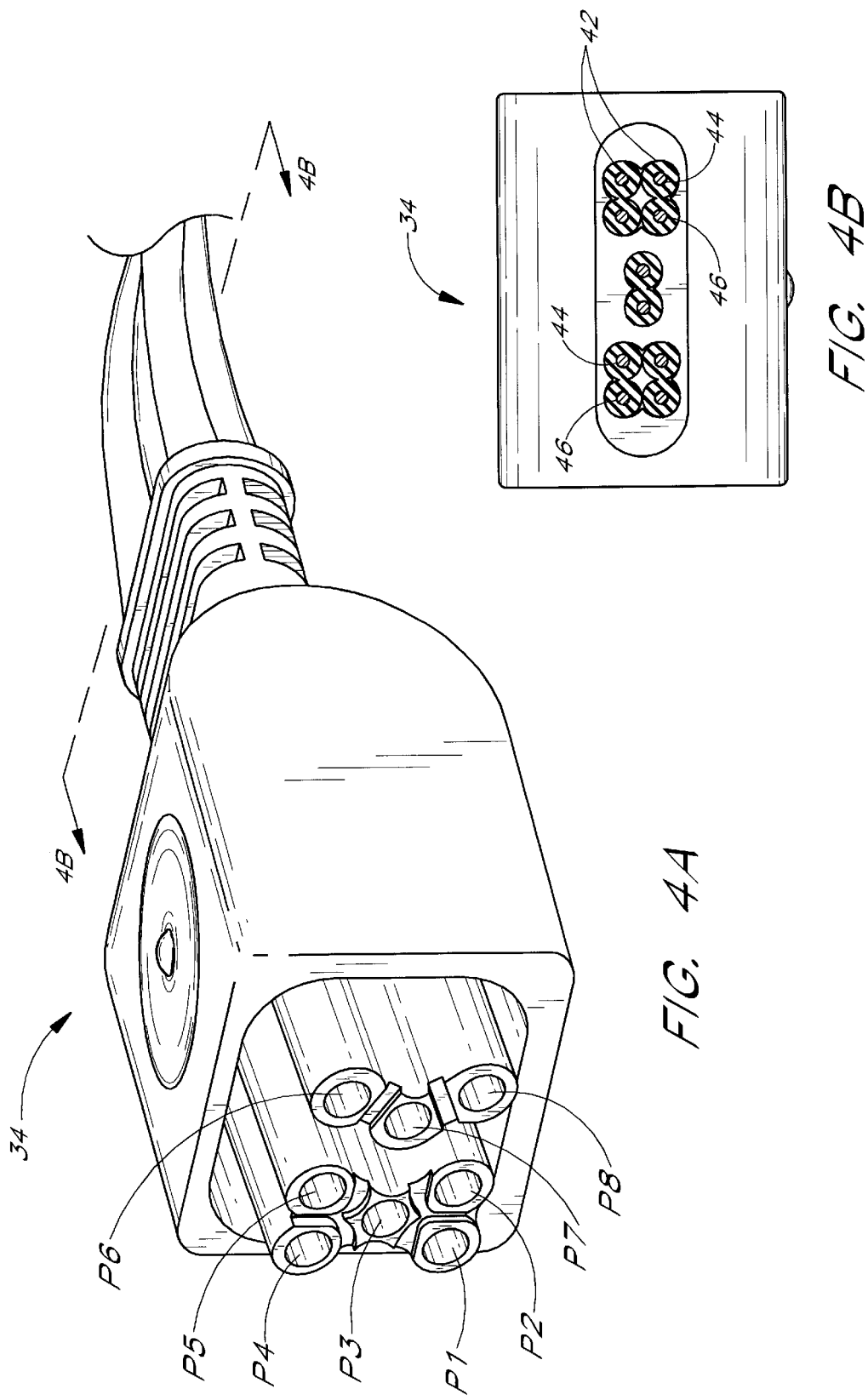

US 6,716,165 B1

PATIENT TELEMETRY DEVICE AND LEADSET DESIGNS FOR PROVIDING ANTENNA DIVERSITY

RELATED APPLICATION

This application claims the benefit of U.S. Provisional Appl. No. 60/273,136, filed Mar. 2, 2001, titled REMOTE TRANSCEIVER AND LEAD SET DESIGNS FOR MEDICAL TELEMETRY.

FIELD OF THE INVENTION

The present invention relates to telemetry systems for remote patient monitoring. More specifically, the invention relates to the use of leads, such as ECG (electrocardiograph) leads, to provide antennas for ambulatory or other remote telemetry devices.

BACKGROUND OF THE INVENTION

A variety of patient monitoring systems exist that allow the physiologic data of patients within a medical facility to be monitored remotely using wireless communications. These systems commonly include remote transmitters or transceivers that collect, and transmit over a wireless channel, the physiologic data of respective patients. This physiologic data may include, for example, real-time electrocardiograph (ECG) waveforms, $SpO_2$ levels, and non-invasive blood pressure readings. The transmitted physiologic data is conveyed to one or more centralized monitoring stations within the medical facility. From such a monitoring station, a clinician can visually monitor the physiologic status, in real time, of many different patients. The monitoring stations may also run automated monitoring software for detecting and alerting personnel of certain types of physiologic events, such as the occurrence of a cardiac arrhythmia condition.

To enable patients to be monitored while ambulatory, some systems include battery-powered remote transceiver devices that are adapted to be worn by or attached to patients while ambulatory ("ambulatory transceivers"). Each ambulatory transceiver attaches to a patient by a pouch or other attachment device, and senses the patient's physiologic data via a set of ECG leads (and/or other types of sensor leads). In one common design, each lead wire of the ECG lead set is constructed of a shielded wire (typically coaxial) comprising an inner conductor surrounded by a mesh shield. The inner conductor electrically connects an ECG sensor to the ambulatory transceiver's sensor circuitry, and is used to carry ECG signals. The outer shield protects the ECG signals from radio frequency (RF) interference. In other designs, each lead wire is an unshielded, single-conductor wire.

In some prior art designs, selected portions of the ECG lead wires are used as the RF telemetry antenna. For example, in one design in which the lead wires have outer shields that are a fractional length of the total wire length, the shields of multiple lead wires are connected together to form the antenna. In another design, the multi-strand conductor of the RL (right leg) lead wire is used as the antenna. An important benefit of these designs is that they eliminate the need for a dedicated antenna mounted to or inside the transceiver's housing. In addition, a lead antenna can provide a somewhat larger aperture, and thus better RF link performance, than a housing mounted antenna.

SUMMARY

One problem with existing designs is that the coaxial ECG lead wires tend to be relatively stiff in comparison to other types of wires. As a result, the leads cause discomfort to patients and tend to lack durability.

Another problem with existing designs, and particularly with ambulatory transmitter and transceiver designs, is that data transmissions are highly susceptible to attenuation caused by the patient's body or nearby objects. This problem is frequently experienced when the patient is in bed. For example, if the patient rolls over on top the antenna (dedicated or ECG lead), the patient's body may block signal transmissions to and from the ambulatory device. Further, the patient's position in bed may cause a portion of the antenna to be positioned close to a bed rail or other grounded metal object, causing the entire antenna to de-tune. In these situations, the patient's real time physiologic data typically can not be remotely monitored with sufficient reliability.

Yet another problem with existing telemetry devices, and other types of devices that receive signals from an ECG lead set, is that they do not provide an adequate solution to the problem of protecting against defibrillation pulses. For example, some designs merely use current-limiting resistors connected along the ECG signal lines. These resistors tend to be large, high-power components, and tend to increase the manufacturing cost of the device while providing only limited protection.

The present invention addresses these and other problems with prior art designs by providing several inventive features that may be used individually or in appropriate combination. One such feature involves the replacement of some or all of the conventional lead wires with lead wires having two side-by-side conductors. In each such lead, one of the two conductors is used to carry ECG signals, and the other is used as an antenna element. An important benefit of this design feature is that the leads are generally more flexible, and lighter in weight, than coaxial leads. As a result, the leads provide greater comfort to patients. Further, in comparison to typical lead wire antenna designs in which the coaxial shield extends only a few inches, the use of an antenna conductor that extends substantially the entire length of the lead wire (as in the preferred embodiment) provides improved antenna performance. Additional benefits include greater lead durability and lower cost of lead material. This and the other features of the invention may also be used with other types of lead sets for sensing physiologic data, such as EEG lead sets and leads sets with SpO2 and oscillometric blood pressure sensors.

Another feature involves statically or dynamically dividing the set of ECG or other leads into two or more groups to provide two or more corresponding telemetry antennas. For example, in a lead set with five ECG leadwiress, the antenna portions of the RL (Right Leg) and C (Chest) leads may be electrically connected to form a first antenna, and the antenna portions of the LA (Left Arm), LL (Left Leg) and RA (Right Arm) leads may be interconnected to form a second antenna. The leads may, for example, be constructed with conventional coaxial lead wires in which the outer shields are used as the antenna portions, or may be constructed with wires having side-by-side conductors as described above. To provide diversity, a control circuit within the transceiver selects between the multiple antennas, preferably based on observed characteristics of received RF transmissions. Thus, for example, when one antenna produces data errors as the result of a lead touching a bed rail, the control circuit may switch to an antenna that does not use the affected lead. In embodiments in which the telemetry device transmits but does not receive data via the antenna used to transmit, the antenna diversity may be selected using antenna impedance measurements (as described below). Alternatively, the telemetry device may simply transmit the same data separately using each antenna to provide redundant transmissions.

In one embodiment, the ECG leads are statically grouped to form the multiple antennas—preferably by fixed electrical connection of antenna conductors within the lead set's connector plug. In another embodiment, the antenna portions of the ECG leads are connected to an electrical switch, such as a matrix switch capable of selecting any combination of one or more ECG leads to use as the antenna. The switch is controlled by a control circuit that dynamically selects the one or more leads to use to form the antenna based on observed signal characteristics and predefined selection criteria.

Another feature, which may be used alone or in combination with the above-mentioned features, involves the use of an impedance detector to monitor the impedance of an ECG-lead antenna (or an antenna that includes conductors within other types of leads). The output of the impedance detector may be used to control an impedance matching circuit to maintain the ECG lead antenna in a tuned state. For example, when the antenna's impedance changes as the result of proximity to a bed rail, the antenna's impedance matching circuit may be dynamically adjusted to maintain the antenna in an optimal state.

The antenna impedance measurements may additionally or alternatively be incorporated into the decision logic used to select an antenna. For example, in one embodiment, an impedance detector is integrated with the above-mentioned matrix switch, and is used to separately monitor the impedance of the antenna portion of each ECG or other lead. These impedance measurements are used (preferably in combination with received signal-quality measurements) to select the lead or leads to use to form the antenna. For example, when the impedance associated with a particular lead falls outside of a predefined range, that lead may automatically be excluded from potential use as or within an antenna.

Another feature of the invention involves using the multiple antenna conductors of the coaxial or non-coaxial leads as elements of a phased antenna array. In one embodiment of a transceiver system, each such antenna conductor is coupled to a respective phase shifter capable of adjusting the phases of signals received and radiated by that antenna conductor. During receive events, a phase detection circuit monitors the phases of the respective RF signals received by the antenna conductors, and controls the phase shifters to compensate for phase differences. During transmission events, the phase shifters are used to effectively steer the beam formed by the antenna array in the direction of a receiving station and/or to reject an interference source. The antenna beam may also be steered passively (without transmitting) to locate a base station.

Another inventive feature, which similarly may be used alone or in combination with the aforementioned features, is an improved circuit for protecting the remote transceiver's circuitry, or the circuitry of another type of device that receives signals from an ECG lead set, from damage caused by defibrillation pulses. In a preferred embodiment, the circuit includes a low capacitance, transient voltage suppression (TVS) circuit connected between the ECG signal path and ground, and further includes a current-limiting resistor connected in-line along the signal path. Separate protection circuits of this type may be provided along each ECG signal path. The use of low capacitance TVS circuits allows small, low cost, surface-mount current limiting resistors to be used in place of the relatively large current-limiting resistors used in conventional designs.

BRIEF DESCRIPTION OF THE DRAWINGS

These and other inventive features will now be described with references to the following drawings.

FIG. 4A illustrates the configuration of the connector plug of the ECG lead set.

FIG. 4B is a cross sectional view taken along the line 4B—4B of FIG. 4A, showing the arrangement of five dual-conductor lead wires extending outward from the connector overmolding.

Figure 1B:
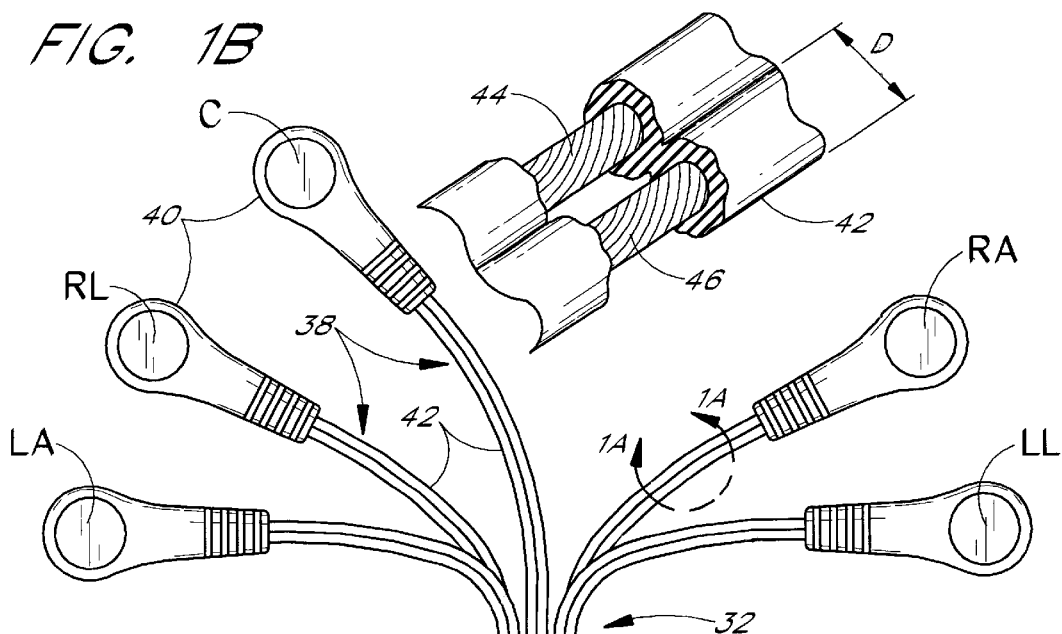
FIG. 1B is a broken-away view taken along line 1A—1A of FIG. 1B, showing the inner construction of a representative lead wire.

Throughout the drawings, reference numbers are reused to indicate correspondence between referenced components.

DETAILED DESCRIPTION OF ILLUSTRATED EMBODIMENTS

An ambulatory transceiver system that embodies some of the inventive features mentioned above will now be described with reference to FIGS. 1–6. Additional designs incorporating other inventive features will then be described with reference to FIGS. 7–9. As will be apparent, many of the disclosed features can be used or practiced independently of others, and without many of the implementation-specific details set forth herein. In addition, many of the inventive features that are described separately can be appropriately combined within an ambulatory or other telemetry device.

Although the specific embodiments illustrated in the drawings involve a transceiver unit that attaches to an ECG lead set, many of the disclosed features may be embodied within or used with other types of devices. Examples of other devices include patient telemetry devices that are merely RF transmitters and not RF receivers (referred to herein as "unidirectional transmitters"), and devices that sense physiologic data other than ECG data. Specific examples of embodiments that involve alternative device types are set forth in the text below.

Throughout the following description, the term "coaxial" refers generally to the positional relationship between conductors (i.e., an inner conductor extends within an outer, tubular conductor). The term "coaxial wire" or "coaxial cable" additionally implies that the inner conductor and outer conductor are separated by a dielectric core. The term "shielded wire" refers to a wire in which the inner and outer conductors are arranged coaxially and may, but need not, be separated by a dielectric core (i.e., a shielded wire may, but is not necessarily, a coaxial wire).

FIGS. 1–6 illustrate the design of an ambulatory transceiver 30 and ECG lead set 32 according to a preferred embodiment of the invention. The ambulatory transceiver 30 is a portable, battery-powered telemetry device adapted to be worn by an ambulatory or non-ambulatory patient. The device 30 operates generally by receiving the patient's ECG signals via the lead set 32, and transmitting the ECG signals in real time via RF as packetized data. The device 30 may also monitor and transmit other types of physiologic data of the patient via additional leads or sensors (not shown), such as respiration signals, SpO$_2$ levels, and NIBP (non-invasive blood pressure).

In one implementation, the ambulatory transceiver 30 is designed to communicate bi-directionally with access point transceivers ("access points") positioned throughout patient areas of a medical facility, as described generally in U.S. Pat. No. 5,944,659, and co-pending U.S. application Ser. No. 09/615,362, filed Jul. 13, 2000, the disclosures of which are hereby incorporated by reference. In other embodiments, the ambulatory transceiver 30 may communicate with a different type of base station, such as a PC with an RF modem. Thus, as used herein, the term "base station" is intended to refer generally to any type of device that receives telemetry data from a remote transceiver by wireless communications.

Figure 1A:
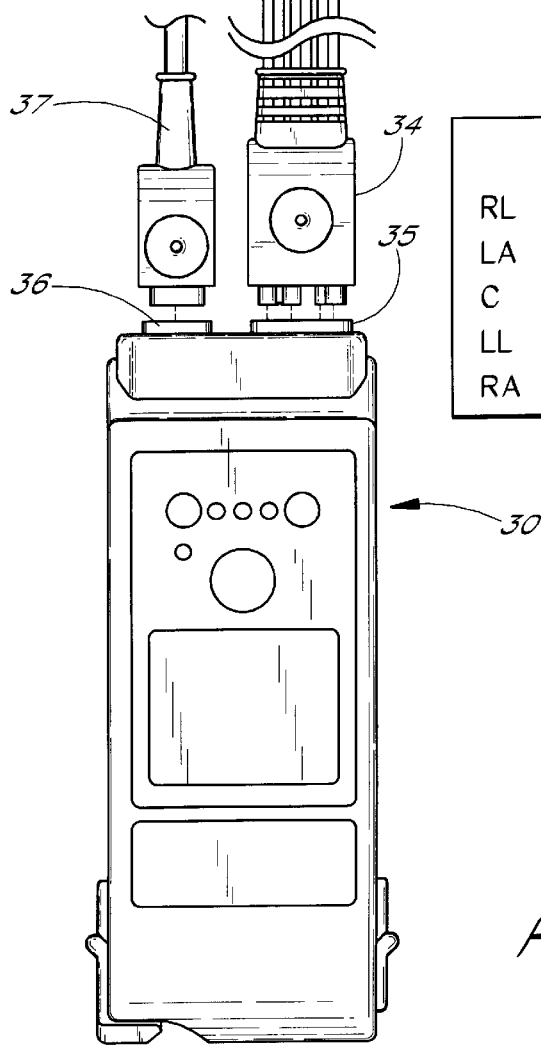
FIG. 1A illustrates an ambulatory transceiver device and representative ECG lead set according to a preferred embodiment of the invention.

As illustrated in FIG. 1A, the ambulatory transceiver 30 includes a lead set connector 35 that receives a connector plug 34 of the ECG lead set 32. The physical configuration of the connector plug 34 is illustrated in FIGS. 4A and 4B (discussed below). In other embodiments, the lead set may be fixedly attached to the transceiver 30 or other transmitting device.

The ambulatory transceiver 30 also includes an input/output (I/O) connector 36 that receives the plug 37 of an I/O cable. The I/O connector 36 allows the ambulatory transceiver 30 to be connected, if desired, to an external device having a standard RS-232 port (or a port which uses another interface standard), such as a mobile blood pressure sensor, an infusion pump, a ventilator, or a PDA (personal digital assistant). Physiologic or other data received from the external device is transmitted by the ambulatory transceiver 30 together with the patient's ECG waveforms, allowing such data to be remotely monitored in real time. The I/O connector 36 may also be used to upload code updates and perform other maintenance related tasks.

I. Lead Set Construction

In the embodiment shown in FIGS. 1–4, the lead set 32 has five leads 38 for sensing ECG signals from the standard left arm, right leg, chest, right arm and left leg positions. Lead sets with three, four, and six leads are also provided for use with the same ambulatory transceiver 30, as described below and illustrated in FIGS. 5C–5G. Each lead 38 of the illustrated lead set 32 is terminated with a snap connector 40 (FIG. 1A) for attachment to an ECG electrode on the patient's skin. Other types of electrode connectors, such as pinch clip connectors, may also be used. Leads or sensors for sensing other types of physiologic data may optionally be included within the same lead set 32.

In accordance with one feature of the invention, each ECG lead 38 is constructed with an insulated wire 42 having two, multi-strand conductors 44, 46 (FIG. 1B) positioned generally parallel to one another in a non-coaxial arrangement from the connector plug 34 to the electrode connector 40. One of the two conductors 46 in each lead 38 is used to carry the patient's ECG signal. This ECG conductor 46 is electrically connected to the conductive contact portion (not shown) of the electrode connector 40. The other conductor 44 is used as an antenna element for providing a telemetry antenna (referred to herein as an "ECG-lead antenna"). As described below, the antenna conductors 44 of multiple leads 38 may optionally be connected to form a multiple-lead antenna. In addition, two or more separate ECG lead antennas may be formed to provide antenna diversity.

In the illustrated embodiment in which the telemetry unit is a transceiver 30, the ECG-lead antenna or antennas are used for bi-directional RF communications with one or more base stations. The ECG-lead antennas may also be used to communicate with other types of devices, such as beacons or chirpers used to monitor patient location. Each antenna conductor 44 has a free end (not shown) terminated within the insulating material or free air space of the corresponding electrode connector 40. Although the terms "ECG conductor" and "antenna conductor" are used herein, it should be understood that these conductors may also be used for other purposes. In embodiments in which the telemetry unit is a unidirectional transmitter, the ECG-lead antennas are used only for transmitting data.

The use of a lead wire 42 in which the conductors 44 are arranged side-by-side, rather than coaxially as in conventional systems, advantageously allows wires with greater flexibility to be used. As a result, a greater degree of patient comfort and lead durability can be achieved. This implementation has also been found to produce improved antenna performance over designs in which the antenna is formed from the outer shields that extend along a small portion of each lead wire. This feature of the design may, but need not, be implemented in combination with an antenna diversity scheme as described below. The characteristics of the lead wires 42 used in one embodiment are listed in Table 1.

TABLE 1

Example Lead Wire Construction

| | |
|---|---|
| Wire Type | bonded 2-conductor cable |
| Conductor (44, 46) | Tinsel with seven cores of Kevlar, each with a single serve metal wrap of silver plated tinsel (T-3922) |
| Insulator | Medical grade polyurethane, temp. rating +105 deg. C. to −25 deg. C. |
| Outer diameter (D in FIG. 1A) | 0.080 inches |
| Max resistance | 0.210 ohms/foot |
| Min. break load | 40 lbs. |

Lead wires constructed as set forth above may also be incorporated into leads and lead sets for monitoring other types of physiologic data. For instance, the same or a similar lead wire construction may be used within an electroencephalogram (EEG) lead set (in which case the ECG electrodes would be replaced with EEG electrodes), or within a lead having an oscillometric blood pressure sensor. As with the ECG lead set described above, one of the side-by-side conductors carries the patient's physiologic data signal to the RF transmitter or transceiver, and the other is used as an antenna element for telemetry. The antenna diversity scheme described in the following section may also be used with such alternative lead and lead set types.

II. Antenna Diversity Using Multiple ECG-Lead Antennas

Another feature of the invention, referred to herein as ECG lead antenna diversity, involves providing two or more separate ECG-lead antennas, and switching between these antennas to provide spatial antenna diversity. This feature is implemented in the preferred embodiment using ECG leads with non-coaxial, unshielded lead wires 42 of the type illustrated in FIG. 1. The ECG lead antenna diversity feature may also be implemented using ECG leads with other types of lead wires, such as with coaxial or other shielded lead wires in which case the outer shields may be used for the antennas. The two or more antennas are preferably formed by effectively dividing the complete set of leads into two or more corresponding, mutually exclusive subsets of leads.

Figure 2:
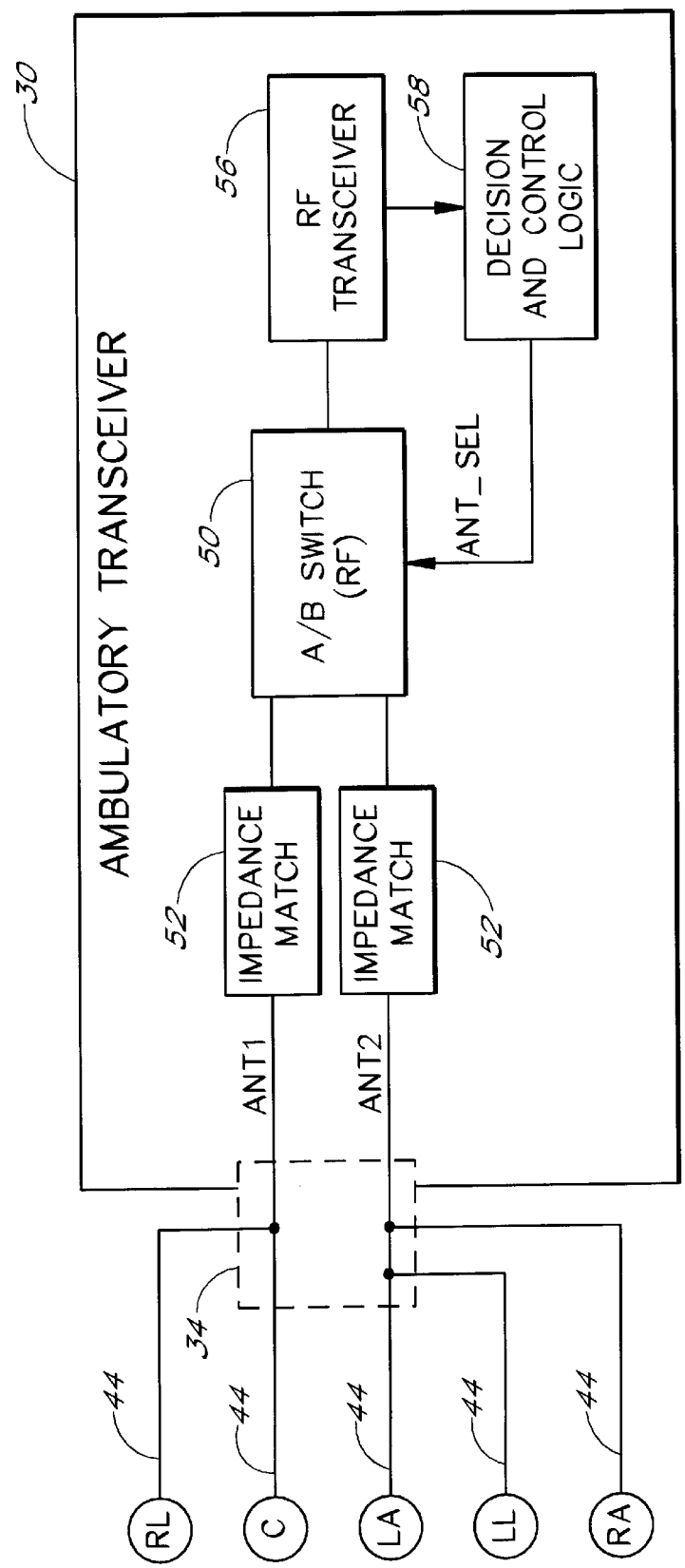
FIG. 2 illustrates an antenna diversity feature of the ambulatory transceiver device and ECG lead set of FIG. 1.

FIG. 2 shows, for a 5-lead set 32 of the type shown in FIG. 1, how the ECG lead antenna diversity feature is implemented in the preferred embodiment. The drawing is also representative of implementations in which coaxial or other shielded ECG lead wires are used. Specifically, the illustrated antenna conductors 44 can be the shields of coaxial or other shielded lead wires; these shields may extend along the entire length of each lead wire, or along only a portion of each lead wire. The ECG conductors 46 are omitted from FIG. 2 to simplify the drawing.

Figure 3:
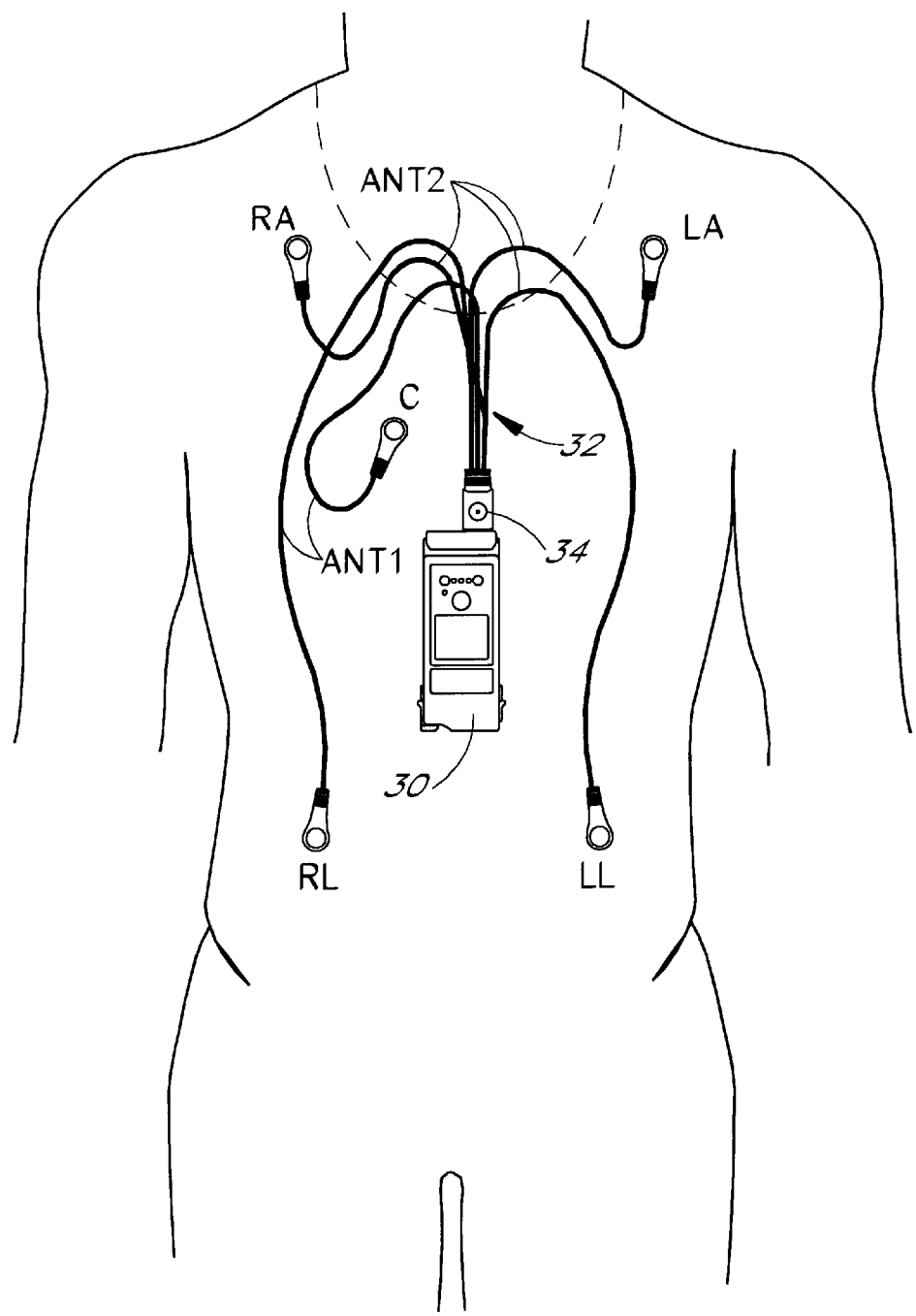
FIG. 3 illustrates the general positions and configurations of the antennas of FIG. 2 when the ambulatory transceiver device and representative lead set are attached to a patient.

In this embodiment, the antenna conductors 44 of the Chest and Right Leg leads 38 are electrically connected to form a first antenna, ANT1; and the antenna conductors of the Left Arm, Left Leg and Right Arm leads are electrically connected to form a second antenna, ANT2. These connections are preferably made inside the connector plug 34, as shown, so that only two antenna connections are needed between the connector plug 34 and the connector 36. The general configurations and positions of the antennas during patient monitoring are depicted in FIG. 3. As discussed below, although the connections between antenna conductors 44 are fixed in this embodiment, switched connections may alternatively be used so that the antennas may be formed or defined dynamically.

As further depicted in FIG. 2, each antenna line ANT1, ANT2 is connected to an RF antenna switch 50 via a respective impedance matching circuit 52A, 52B. In one implementation, the impedance matching circuits 52A, 52B match the approximately 600 ohm impedance of the ECG-lead antennas ANT1, ANT2 with the approximately 50 ohm impedance of the printed circuit boards used within the ambulatory transceiver 30. The impedance matching circuits may be omitted in embodiments that use coaxial leads. In addition, as discussed below, dynamically controlled impedance matching circuits may be used to compensate for changes in antenna impedances.

The antenna switch 50 selects between the two antennas, ANT1 and ANT2, and connects the selected antenna to an RF transceiver circuit 56 ("RF transceiver"). The RF transceiver 56 uses the currently selected antenna both to receive and transmit RF data packets. The RF transceiver 56 includes or is connected to a decision and control logic circuit 58 that controls the switch 50 via a selection signal, ANT_SEL. This circuit 58 preferably selects between the antennas based on information about received signal transmissions. This information may, for example, include one or more of the following: signal strength measurements, data indicating whether transmissions are being received error-free, and impedance measurements of antennas or antenna elements. The circuit 58 may also select between the antennas based on the quality of the signal received from the transceiver 30 by a base station, as reported back to the transceiver by the base station.

As will be apparent to those skilled in the art, a number of variations to the design shown in FIG. 2 are possible. For example, each antenna could be formed from a different set of antenna conductors 44 than those shown (e.g., the RL lead can be used for the first antenna, and the LA, C, LL and RA leads can be used for the second antenna). In addition, the ECG leads 38 could be grouped or divided to provide three, four, or five separate antennas, rather than two. Further, rather than using "fixed" antennas as shown, the antenna conductors 44 could be connected to a switch (as in FIG. 8, discussed below) that dynamically selects the ECG lead or leads 38 to use as the antenna. In addition, each of the two or more antennas could be connected to its own, respective RF receiver circuit to allow the antennas to receive data transmissions concurrently, so that a packet will be successfully received if any of the antenna-receiver pairs successfully receives the packet. Further, the A/B type switch 50 may be replaced with a switch capable of connecting the two fixed antennas to form a third antenna option, ANT3=ANT1+ANT2.

Further, one or more additional antenna conductors may be provided outside the leads themselves for use as additional antenna elements. For example, an antenna wire may be bonded to or dangled from the plastic housing of the transceiver 30, and may be incorporated into one or more of the ECG lead antennas as an additional element.

Any of a variety of antenna selection methods may be used in the system of FIG. 2. For example, in one embodiment, whenever the RF transceiver 56 fails to successfully receive a packet expected from an access point (e.g., detects a CRC error), the circuit 58 automatically switches to the other antenna; this antenna is thereafter used until another packet is missed. In another embodiment, at the beginning of each base station transmission (which occurs during a predefined timeslot of a TDMA frame in the preferred embodiment), the ambulatory transceiver 30 samples the signal strength of the received signal on one antenna (ANT1 or ANT2) and then the other. The antenna having the higher signal strength is then selected for use—both to receive the packet transmitted by the base station and to transmit the next packet—unless a packet was missed with that antenna on the immediately preceding TDMA frame.

In addition, in embodiments in which frequency hopping is used, the ambulatory transceiver 30 may perform a separate antenna selection analysis for each frequency of the hopping sequence. The antenna selections would thus reflect frequency dependencies that may exist. As discussed below with reference to FIGS. 7 and 8, the antenna may alternatively be selected in-whole or in-part based on antenna impedance measurements. In addition, the antenna could be selected based in-whole or in-part on feedback from an access point or other base station with which the ambulatory transceiver 30 communicates. Further, in embodiments in which each base station has two antennas, A and B, a protocol may be used in which the ambulatory transceiver 30 samples the signal strength for each of the four possible antenna combinations (A:1, A:2, B:1 and B:2), and selects the antenna combination that produces the best result.

Rather than selecting between the available antennas based on measurements, the transceiver may be designed to simply transmit each packet of physiologic data on each antenna to provide redundancy. For example, if two antennas are provided, the transceiver could transmit each packet using antenna A and then antenna B to provide a combination of time and space diversity. In one such embodiment, each access point or other base station has two antennas/diversities, such that each transmission can take four possible paths. Yet another approach is to use one antenna as the transmit antenna, and another antenna as the receive antenna.

In embodiments in which the telemetry unit is a unidirectional transmitter, the transmitter may select between the multiple ECG-lead antennas based solely on antenna impedance measurements. Alternatively, the transmitter could simply transmit the patient's data separately using each ECG lead antenna, as described above.

Antenna diversity as set forth above may also be implemented using leads and lead sets for sensing other types of physiologic data, including EEG lead sets, leads with oscillometric blood pressure sensors, and leads with $SpO_2$ sensors. For instance, in a 2-lead set in which one of the leads senses $SpO_2$ levels and the other lead senses blood pressure, two single-lead antennas may be provided, each of which is formed from a conductor within a respective lead. The telemetry unit may use any appropriate antenna switching method, including those described above, to switch between these two antennas.

III. ECG Connector Plug and Example Antenna Connections

FIG. 4A illustrates the configuration of the connector plug 34 in further detail. The plug includes eight contacts, labeled P1–P8, for connecting with eight corresponding contacts (not shown) on the connector 35. In one embodiment, the plug 34 is a custom bulkhead connector mating connector with a Bayer Makroblend EL700 connector shell, socket contacts, and a Santoprene overmold that meets EN 529–1989 IPX7 requirements. FIG. 4B, which is a cross sectional view taken along line 4B—4B in FIG. 4A, further illustrates the connector plug 34 and the lead wires 42 for the 5-lead embodiment of FIGS. 1–3.

Figure 5A:
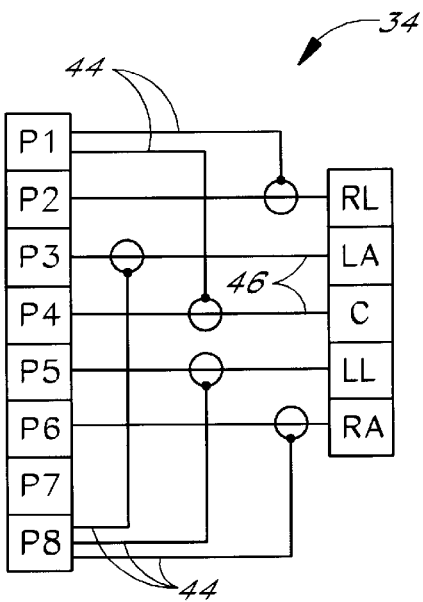
FIGS. 5A–5G illustrate the electrical connections within the connector plug of FIG. 4 for each of seven different ECG lead sets that may be used with the ambulatory transceiver device.

In the preferred embodiment of the transceiver system, the same connector plug design is also used within other ECG lead set configurations. FIGS. 5A–5G illustrate the electrical connections within the connector plug 34 for each of the seven ECG lead set configurations. All of these lead sets provide two, fixed antennas, and may be used with the same ambulatory transceiver device 30 (e.g., a device with the antenna selection circuit depicted in FIGS. 2 and 6). FIG. 5A illustrates the interconnections used to implement the antenna design shown in FIG. 2. In this embodiment, the antenna conductors 44 of the RL and C leads are connected to P1, and the antenna conductors of the LA, LL and RA leads are connected to P8. The remaining contacts (except for P19, which is unused) carry the patient's ECG signals. The antenna conductors 44 are preferably connected in this and the other illustrated lead set configurations of FIG. 5 by inserting the ends of the corresponding antenna conductors 44 into a common socket contact of the plug 34.

Figure 5B:
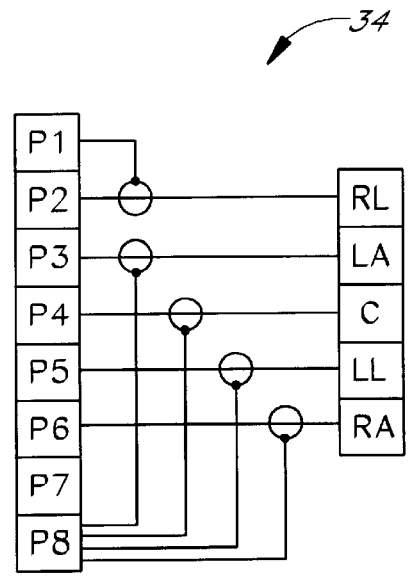
Figure 5C:
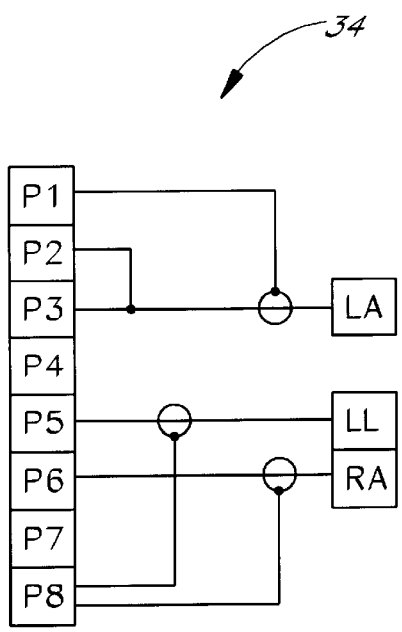
Figure 5D:
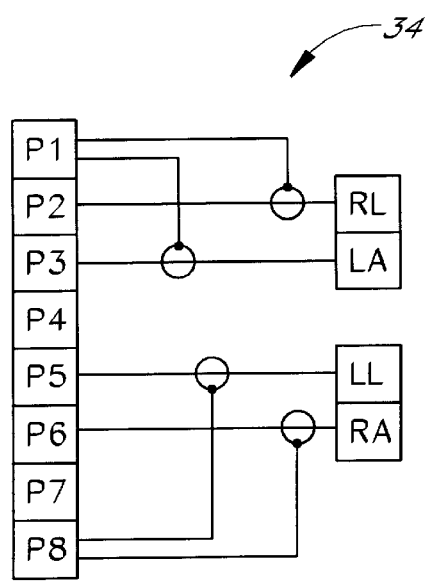
Figure 5E:
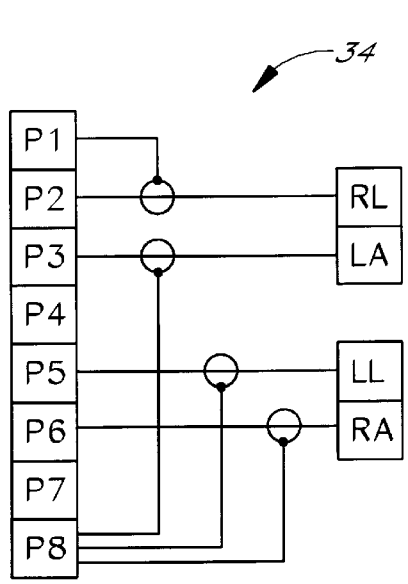
Figure 5F:
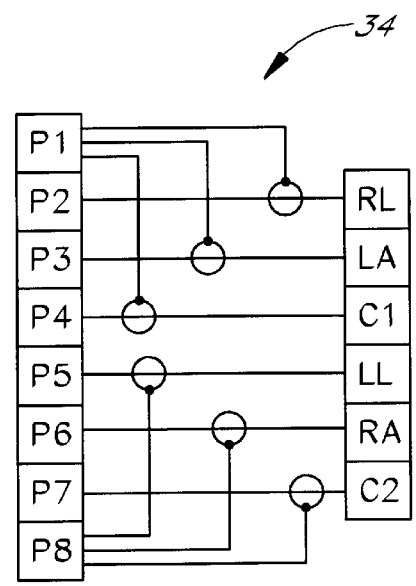
Figure 5G:
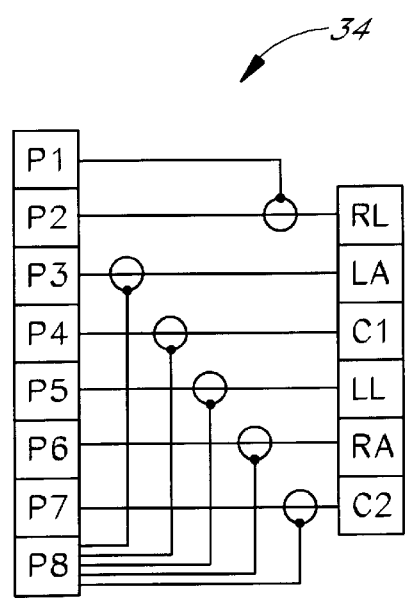

FIG. 5B illustrates a 5-lead set in which the antenna conductor 44 of the RL lead forms the first antenna, and the antenna conductors 44 of the LA, C, LL and RA leads are all connected to form the second antenna. FIG. 5C illustrates a 3-lead set in which the antenna conductor 44 of the LA lead forms the first antenna, and the antenna conductors 44 of the LL and RA leads are connected to form the second antenna. FIG. 5D illustrates a 4-lead set in which the antenna conductors 44 of the RL and LA leads are connected to form the first antenna, and the antenna conductors 44 of the LL and RA leads are connected to form the second antenna. FIG. 5E illustrates a 4-lead set in which the antenna conductor 44 of the RL lead forms the first antenna, and the antenna conductors 44 of the LA, LL and RA leads are connected to form the second antenna. FIG. 5F illustrates a 6-lead set in which the antenna conductors 44 of the RL, LA and C1 (Chest1) leads are connected to form the first antenna, and the antenna conductors 44 of the LL, RA, and C2 (Chest 2) leads are connected to form the second antenna. FIG. 5G illustrates a 6-lead set in which the antenna conductor 44 of the RL lead forms the first antenna, and the antenna conductors 44 of the LA, C1, LL, RA and C2 leads are connected to form the second antenna. Various other configurations are possible, including configurations that provide three or more antennas.

The lead set designs shown in FIGS. 5A–5G preferably use non-coaxial leads 38 of the type shown in FIGS. 1A and 1B. As will be recognized, however, these designs can also be implemented using coaxial lead wires. The use of coaxial lead wires to implement these and other multiple-antenna ECG lead sets is considered part of the present invention.

IV. Transceiver Architecture and Defibrillation Pulse Protection Circuitry

Figure 6:
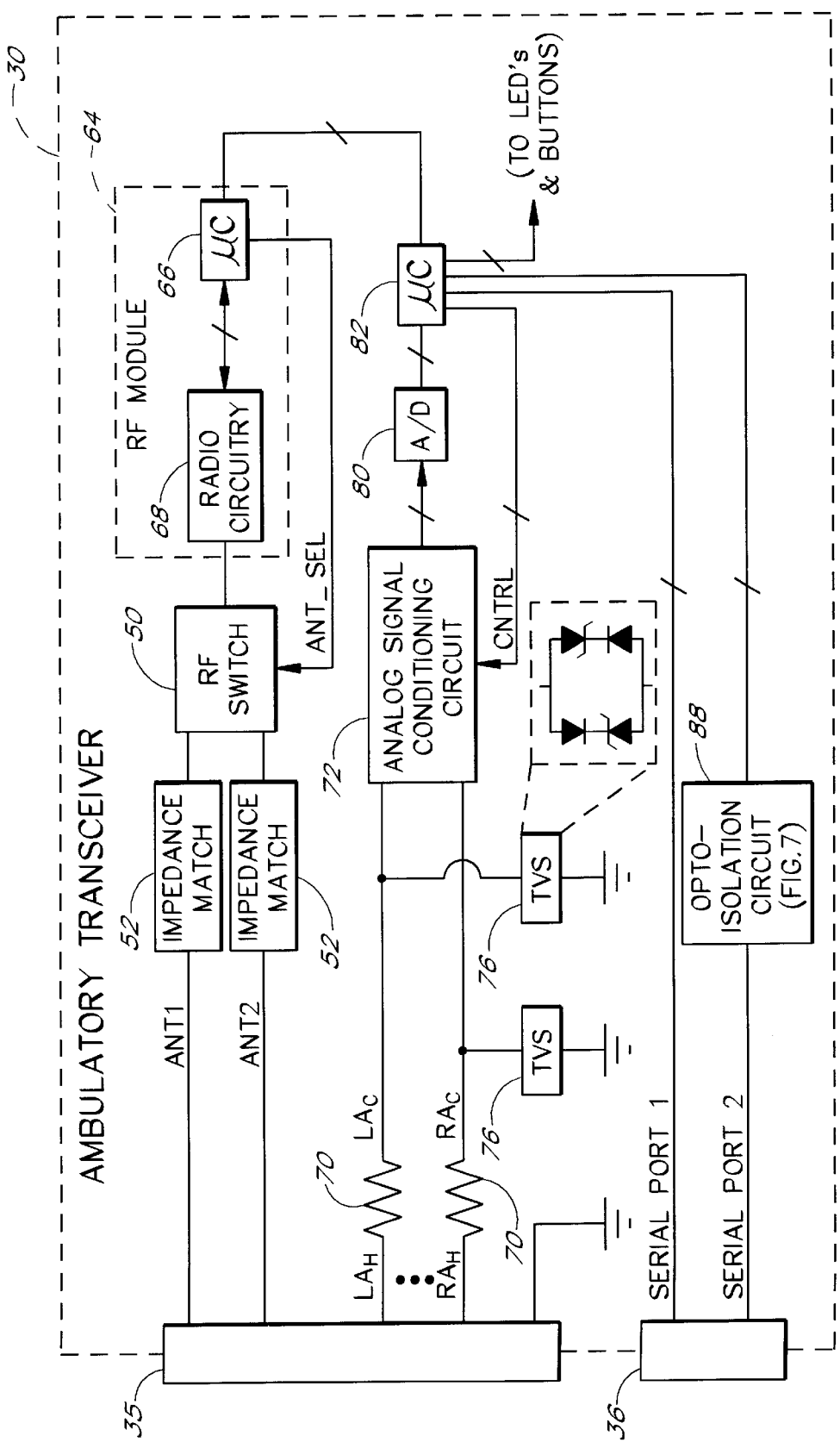
FIG. 6 illustrates the circuitry of the ambulatory transceiver device in further detail.

FIG. 6 illustrates the circuitry of a preferred embodiment of the ambulatory transceiver device 30 in further detail. As mentioned above, this circuit may be used with each of the seven ECG lead sets shown in FIGS. 5A–5G. The circuit may also be used with other lead sets that provide two fixed antennas. In this embodiment, the RF antenna switch 50 is connected to a removable RF module 64. The RF module includes a microcontroller 66, such as an Atmel ATmega 103L with built-in RAM and ROM, and a radio circuit 68. The microcontroller 66 and radio circuit 68 collectively implement the RF transceiver 56 depicted in FIG. 2. As shown in FIG. 6, this microcontroller 66 also generates the control signal ANT_SEL used to select between the two antennas. The task of selecting between the antennas may alternatively be implemented within dedicated hardware, such as an ASIC (application-specific integrated circuit), a separate microprocessor device, or by a combination of devices.

As further depicted in FIG. 6, each ECG conductor 46 (FIG. 1B) of the lead set connects to a respective ECG signal line (LA, RA and RL signal lines shown) within the ambulatory transceiver 30. The RL signal line is connected to ground, as is conventional. The remaining five ECG signal lines (LA, C1, C2, RA, and LL) are connected to an analog signal conditioning circuit 72 via respective current-limiting resistors 70. As discussed below, these current-limiting resistors 70 are preferably surface mount components. Each current-limiting resistor 70 is preferably a single component, but may alternatively be in the form of two or more resistor components connected in series.

Each current-limiting resistor 70 has a "hot" side (designated by the subscript "H") which connects to an ECG conductor 46 of the lead set, and a "cold" side (designated by the subscript "C") connected to the signal conditioning circuit 72. The cold side of each resistor 70 is additionally connected to ground via a respective bidirectional Transient Voltage Suppression (TVS) circuit 76. Each resistor 70 and corresponding TVS circuit 76 form a protection circuit that protects the circuitry of the ambulatory transceiver 30 from potential damage in the event that a defibrillation pulse is applied to the patient. Specifically, when a defibrillation pulse is applied, each TVS circuit 76 opens (becomes conductive), as necessary, fast enough to prevent the voltage on the hot side of the corresponding resistor 70 from exceeding about 1000 volts. The likelihood of damage to the signal processing or other circuitry or the transceiver caused by arcing is thereby reduced. Each resistor 70 provides an additional level of protection by limiting current flow during application of the defibrillation pulse.

In addition to protecting the circuitry of the transceiver 30, the protection circuit protects clinicians that may be in contact with the transceiver from conducting some of the pulse. The protection circuit also reduces the likelihood that some of the defibrillator energy will be "stolen" (reducing the effectiveness of the procedure) as a result of a low resistance path across the ECG lead set.

An important aspect of the protection circuit design involves the use of TVS circuits 76 having a very low junction capacitance—preferably less than 10 pF (picofarads) each, and more preferably less than 5 pF each. Each TVS circuit 76 also preferably has a breakdown voltage of less than 10 volts and an activation time of less than 20 microseconds. In one embodiment, one or more surface mounted USB0812C integrated circuits (TVS arrays) available from Microsemi Corporation are used to provide the TVS circuits 76. The data sheet for the USB0812C device is hereby incorporated herein by reference. The use of such low capacitance, bidirectional TVS circuits 76 advantageously allows the relatively large, high-power (e.g., one Watt), non-surface-mount resistors conventionally used for defibrillation pulse protection to be replaced with the smaller resistors 70, which may advantageously be surface mounted resistors. The size and manufacturing cost of the of the defibrillation protection circuitry can thereby be reduced. Each resistor 70 preferably has a power rating of less than 0.5 Watts. In one embodiment, 90 k ohm, 0.1 Watt surface-mount resistors 70 are used, and are mounted to a printed circuit board (not shown) of the bulkhead connector.

The protection circuit design also provides improved safety in the presence of faults. For example, if either a resistor or a TVS circuit fails, there is still some protection. In contrast, in prior art devices that use a pure resistor protection circuit, if one of the current-limiting resistors fails to a short then there is no protection. This protection circuit design may also be incorporated into other types of electronic devices that receive signals from an ECG lead set, including but not limited to bedside monitors, Holter recorders, diagnostic ECG machines, and portable defibrillators.

As further illustrated in FIG. 6, the analog ECG signal outputs of the signal conditioning circuit 72 are converted to corresponding digital signals by an analog-to-digital (A/D) converter 80. These digital ECG signals are processed by a second microcontroller 82, such as a Mitsubishi M16C/62 device with built-in RAM and ROM, before being passed to the RF module 64 for transmission. This microcontroller 82 is also responsible for the following tasks: (1) controlling the signal conditioning circuit 72; (2) controlling and providing an interface for two serial ports (labeled 1 and 2), which are accessible via the 12-contact data I/O connector 86; (3) driving LEDs on the housing of the ambulatory transceiver 30; (4) detecting and processing button depression events; and (5) detecting fault conditions in the leadset connection (e.g. a poor electrode to skin contact or a failure in the lead conductor).

One of the two serial ports (labeled port 1) is used primarily to upload code updates. The second serial port (labeled port 2) is used to connect the ambulatory transceiver 30 to an external device (typically an AC-powered medical device) having a standard port, such as a port which operates according to one or more of the following interface standards, the specifications of which are hereby incorporated herein by reference: RS-232, RS-422, RS-485, EIA-562, TTL. The ambulatory transceiver 30 transmits the physiologic or other data received from the external device together with the patient's ECG waveforms (preferably within the same packets), allowing such data to be remotely monitored in real time.

V. Opto-Isolation Circuit

As illustrated in FIG. 6, port 2 preferably includes an opto-isolation circuit 88 which isolates the port in accordance with regulation UL-2601. While the external device is connected, the opto-isolation circuit 88 electrically isolates the external device from the ECG lead set, and thus protects the patient from potential shock caused by the external medical device. The opto-isolation circuit thereby allows the transceiver 30 to communicate with the external device and receive ECG signals from the lead set simultaneously.

In accordance with one aspect of the invention, the hot side of the opto-isolation circuit is powered by the external device by stealing power from the RS-232 or other standard port. Conventional power stealing methods may be used for this purpose. An important benefit of using power stealing to power the hot side of the opto-isolation circuit is that it eliminates the need for a separate, isolated power supply.

In one embodiment, the opto-isolation circuit 88 implements a quasi-RS-232 interface that supports a wide range of existing medical devices having RS-232 ports. The opto-isolation circuit 88 may alternatively be entirely RS-232 compliant. In addition, the circuit 88 may be designed to support multiple different interface standards.

In one embodiment, the opto-isolation circuit 88 with power stealing is alternatively incorporated into the cable 37 (FIG. 1) that connects the transceiver 30 to the external device. In this embodiment, separate cables are provided for some or all of the different interface standards (e.g., RS-232, RS-422, RS-485, EIA-562, and TTL), each with a different, interface-specific version of the opto-isolation circuit 88. The appropriate cable can then be selected to match the interface of the external device.

In other embodiments, an opto-electric circuit 88 as described above may be incorporated into or used with other types of patient-attached, battery-powered devices that receive a patient's ECG signals. For example, the circuit 88 can be incorporated into a unidirectional transmitter, a Holter recorder, a mobile ventilator, or a PDA; or may be incorporated into a cable that connects such a device to the external device.

VI. Dynamic Impedance Matching

Figure 7:
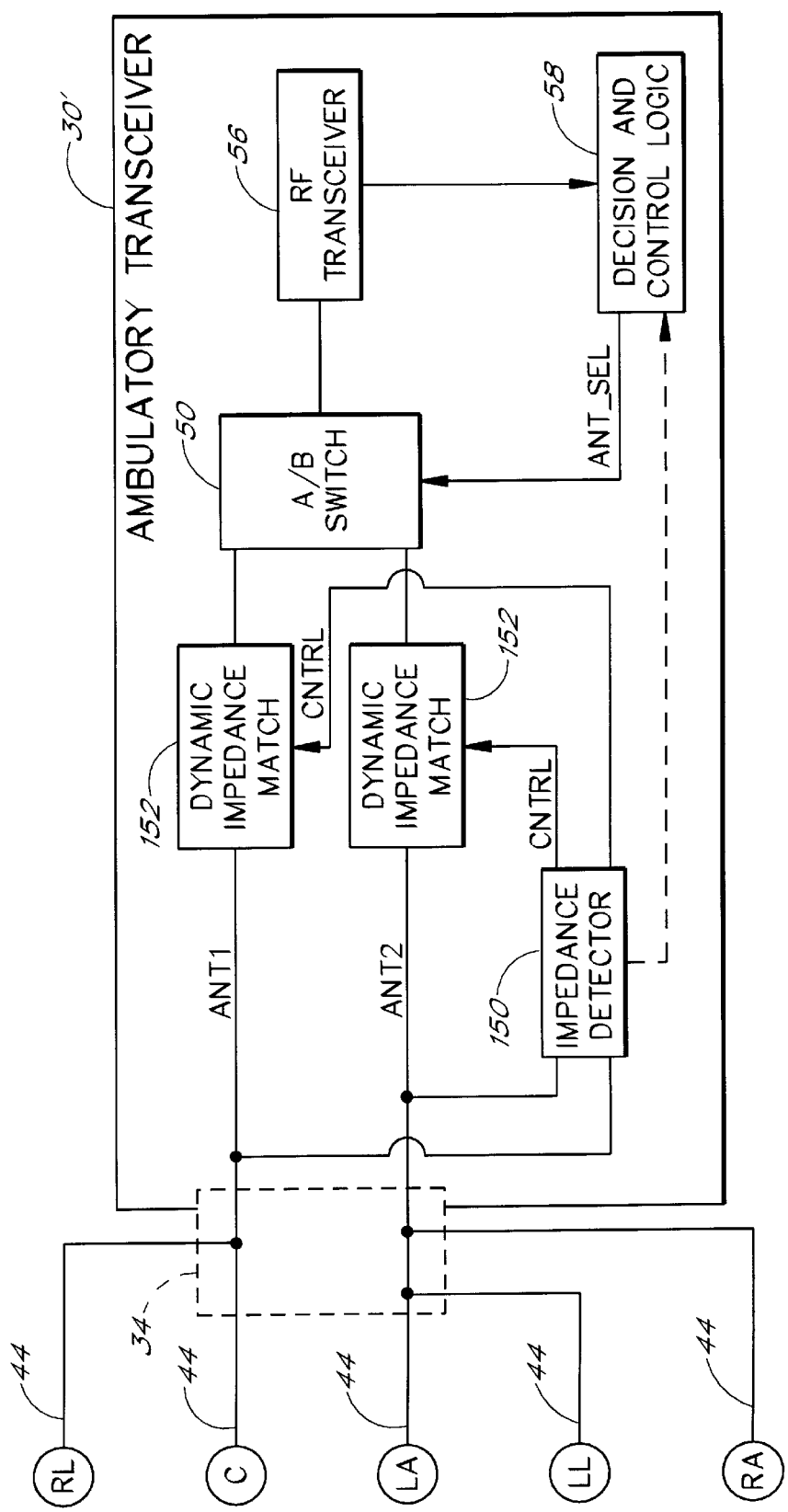
FIG. 7 illustrates a dynamic impedance matching feature that may be added to the ambulatory transceiver design.

FIG. 7 illustrates another inventive feature that may be incorporated into the transceiver design, or into a unidirectional transmitter that uses lead conductors as antenna elements. In this embodiment 30', the impedance matching circuits 152 are dynamically controlled based on real time impedance measurements of the antennas, ANT1 and ANT2. Specifically, an impedance detector 150 monitors the respective impedance of each antenna (e.g., by monitoring signal reflections caused by impedance mismatches), and outputs control signals that reflect these measurements. The control signals are used to dynamically adjust the impedance matching circuits 152, as necessary, to generally maintain proper tuning between the antennas and the transceiver circuitry. Well known impedance matching techniques used in other types of RF applications may be used for this purpose.

In the embodiment shown, the control circuitry for controlling the dynamic impedance matching circuits 152 is included within the impedance detector 150 block. The actual control path for controlling the impedance matching circuits 152 may include a programmed processor, such as one of the microcontrollers 66, 82 shown in FIG. 6. The controller or control circuit may adaptively correct for detected impedance imbalances using a conventional feedback process.

The use of dynamic impedance matching provides additional protection against the effects of bed rails and other sources of antenna detuning. For example, if the impedance of ANT1 drops as the result of a lead being positioned close to a bed rail, the corresponding impedance matching circuit 152 will automatically be adjusted to compensate for the impedance drop. In many cases, this adjustment will be sufficient to maintain the affected antenna in an operable state.

As depicted by the dashed arrow in FIG. 7, the impedance measurements may also be incorporated into the logic used to select between the antennas. For example, when the impedance of an antenna falls outside a pre-selected range, that antenna may automatically be excluded from use.

The use of dynamic impedance matching as described above may also be used in designs that do not provide antenna diversity. For instance, all of the antenna conductors 44 could be connected to form a single antenna; the impedance of this single antenna could then be monitored, and its matching circuit 152 adjusted, in the same manner as described above. Further, although dynamic impedance matching is preferable implemented using leads with unshielded lead wires of the type described above, the feature may also be used with lead sets having coaxial or other shielded lead wires.

The dynamic impedance matching feature as set forth above may also be used with leads and lead sets for sensing other types of physiologic data, including but not limited to EEG, $SpO_2$, and blood pressure data.

VII Dynamic Selection of Antenna Conductors

Figure 8:
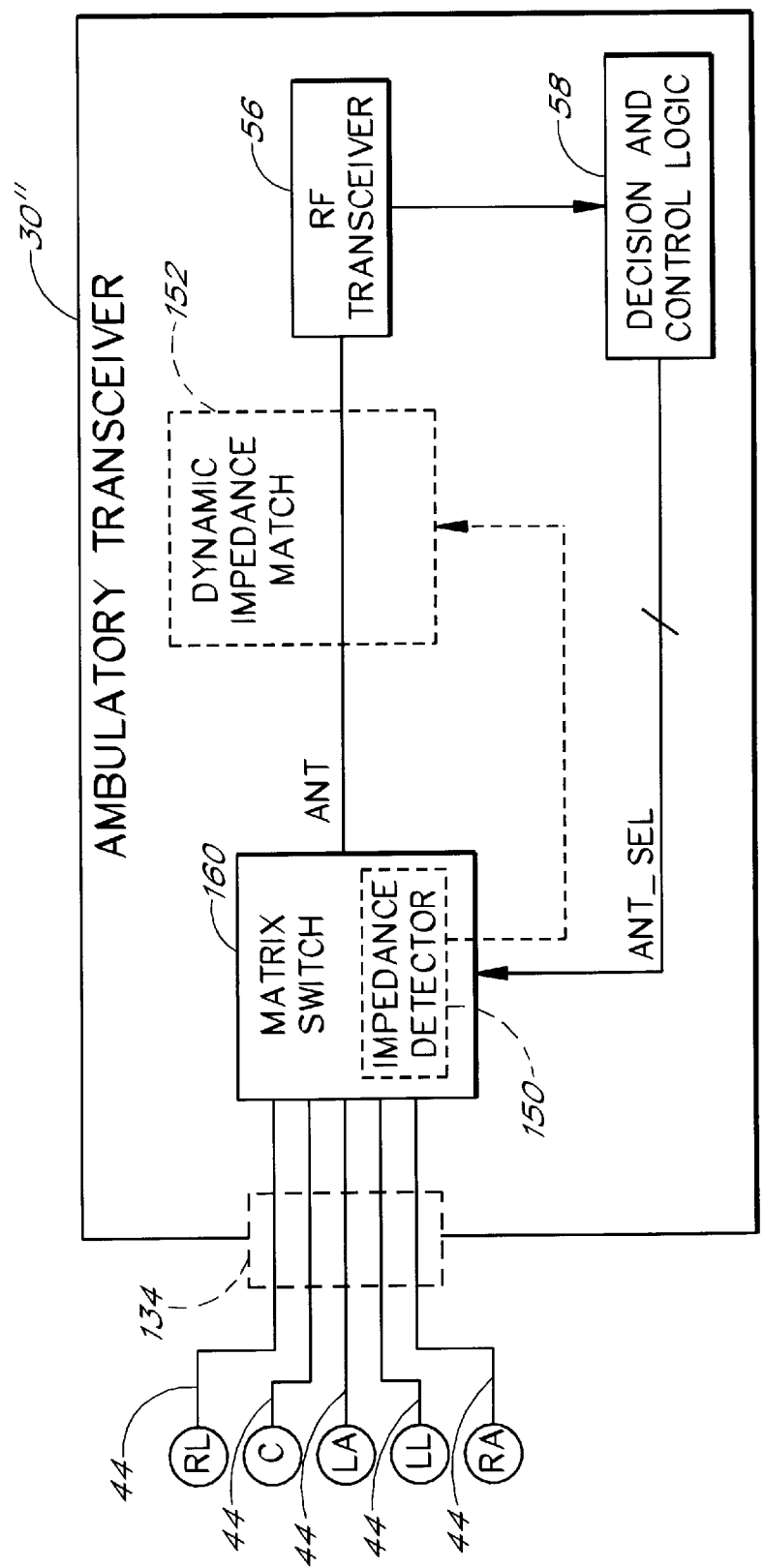
FIG. 8 illustrates the use of a matrix switch to select the ECG lead or leads to use as an antenna.

The ECG-lead antennas illustrated in the preceding drawings are "fixed" or "statically defined," meaning that each antenna is formed using a fixed set of one or more ECG leads. One possible enhancement to the design is to add a switch for dynamically selecting the antenna conductor(s) 44, and any additional antenna elements that may be provided as described above, to use as the antenna. FIG. 8 illustrates one embodiment of this feature. Each antenna conductor 44 is connected to a matrix switch 160 capable of selecting any one or more ECG leads to use as the antenna. For a five-lead set as shown, the switch is thus capable of forming 31 different antennas corresponding to the $2^5-1$ possible combinations of ECG leads. More generally, if the lead set has N antenna conductors (one per lead), the switch can form $2^N-1$ possible combinations. The antenna conductor(s) selected for use as the antenna are connected by the switch 160 as a unit (single antenna) to the RF transceiver 56. In the embodiment shown, the connector plug 134 connects each antenna conductor 44 to a corresponding signal line within the transceiver. Alternatively, the switch 160 could be formed within the connector plug such that fewer connections are needed.

Any of a variety of antenna selection algorithms can be incorporated into the decision and control logic 58 to control the matrix switch 160. In one embodiment, for example, the ambulatory transceiver 30 operates in either a "two-antenna diversity" mode or an "exception" mode, which may be implemented as follows:

Two-antenna diversity mode: While in this mode, the ambulatory transceiver 30 selects between two "default" antennas, ANT1 and ANT2, each of which is formed from a different respective subset of ECG leads (e.g., ANT1=RL and C, and ANT2=LA and LL and RA). Any of the antenna selection methods described above may be used for this purpose. When N consecutive packets are missed, the transceiver switches to the "exception" mode.

Exception mode: Upon entering this mode, the ambulatory transceiver 30 attempts to communicate with the base station using each possible combination of ECG leads 38 as the antenna, according to a predefined sequence. For example, the transceiver may initially use each ECG lead individually, then each possible pair of leads, and then each possible combination of three leads, and so on until all combinations have been attempted. This sequence may be statically defined, or may be based on historical data recorded within the transceiver's memory about the lead combinations that have previously produced a successful result. Once a packet is successfully received, the ambulatory transceiver 30 continues to use the selected antenna, and attempts to revert back to the "two-antenna diversity" mode on every $X^{th}$ attempt to receive a packet. The transceiver switches back to the two-antenna diversity mode when either (1) a packet is successfully received during an attempt to return to the two-antenna diversity mode, or (2) M consecutive packets are missed using the antenna selected in the exception mode.

As a variation of the above approach, the transceiver 30 could use the entire set of ECG leads as the default antenna (i.e., interconnect all of the antenna conductors), and switch to the "exception mode" when a problem is detected with the default antenna (e.g., packets are missed, and/or signal strength falls below a threshold).

As illustrated in FIG. 8, the matrix switch 160 may optionally be integrated with an impedance detector 150' that monitors the impedance of each antenna conductor 44 individually. These impedance measurements may be appropriately incorporated into the antenna selection process. For example, when the impedance of a particular lead's antenna conductor 44 falls below a predefined threshold, the exception mode algorithm may automatically skip over all lead combinations containing that lead. As further illustrated, the impedance measurements may additionally or alternatively be used to control a dynamic impedance matching circuit 152 in the manner described above.

Although all of the antenna conductors 44 are passed through to the switch in the embodiment in FIG. 8, a hybrid approach is also possible in which only some of the antenna conductors 44 are passed through. For example, referring to FIG. 8, the RL and C conductors 44 could be passed through to the switch 160, and the LA, LL and RA conductors 44 could be connected within the plug 134 (fixed connections) and passed to the switch 160 as a single antenna, ANT. The switch 160 could then select between the following seven possible antennas: RL alone, C alone, ANT alone, RL+C, RL+ANT, C+ANT, and RL+C+ANT.

Another variation is to use a matrix switch that has two separate outputs, each of which is connected to a respective receiver. With this configuration, the ambulatory transceiver 30 can receive transmissions using two antennas simultaneously, each of which may be formed from any combination of one or more leads.

The matrix switch embodiment set forth above may also be used with leads and lead sets for sensing other types of physiologic data, such as EEG signals.

VIII. Phased Antenna Array

Figure 9:
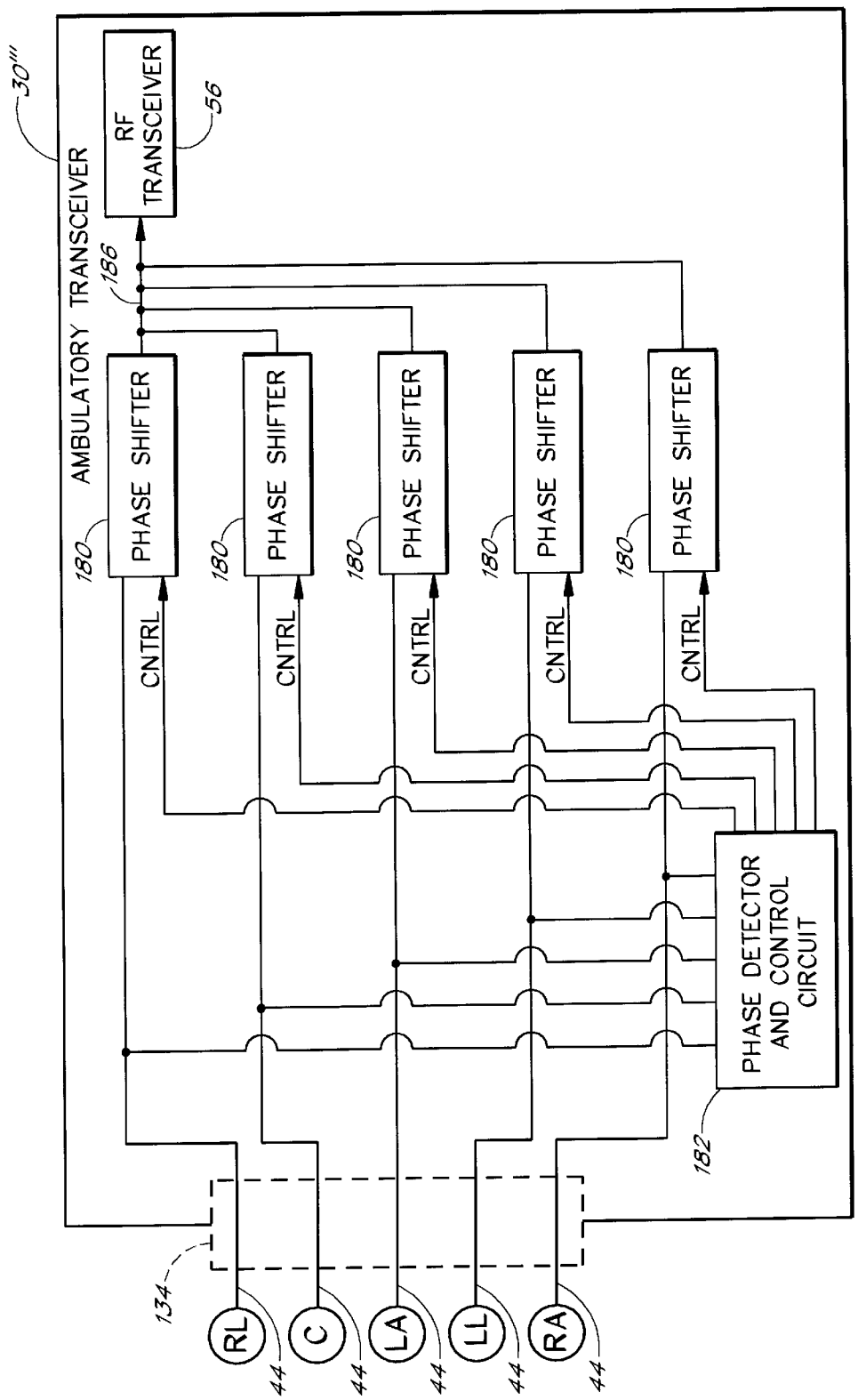
FIG. 9 illustrates an embodiment in which the multiple antenna conductors of the ECG leads are used as elements of a phased antenna array.

FIG. 9 illustrates another feature that may be incorporated into the ambulatory transceiver design to improve performance. In this embodiment, the antenna conductors 44 of at least some, and preferably all, of the ECG leads 38 (and/or other types of leads such as those described above) are used as individual elements of a phased antenna array. One or more additional antenna elements (not shown) may be provided outside the lead set, as described above, to increase the number of elements within the array. As illustrated, each antenna conductor 44 (and each additional antenna element, if any) is coupled to a respective phase shifter 180. The antenna conductors 44 are also connected to a phase detector and control circuit 182 ("controller") which controls the phase shifters 180. The phase shifters 180 are also connected via a common electrical node 186 to the RF transceiver 56.

In one embodiment, each phase shifter 180 can be placed into an "off" mode in which it passes no energy. This is logically equivalent to having a SPST switch in series with the phase shifter, though in practice the two functions may be integrated into the same device. This feature permits an antenna to be formed using less than all of the antenna elements, as may be desirable in some circumstances.

During receive events, the controller 182 measures the differences between the phases of the respective signals received by the antenna conductors 44 (and any additional antenna elements) from the base station. Based on these measurements, the controller 182 adaptively adjusts the phase shifters 180 as necessary to bring these signals into phase with one another. The controller may also place one or more phase shifters 180 in its "off" mode. The phase-adjusted signals are summed at node 186 to produce the RF signal processed by the transceiver 56. During transmission events to the same base station, the same phase shifter settings are used to modify the phase of the transmission signal separately for each antenna conductor 44. The beam is thus effectively steered back in the direction of the base station, improving the likelihood of reception.

In embodiments in which the ambulatory transceiver 30 concurrently monitors transmissions from multiple devices (e.g., to evaluate candidate access points with which to establish a connection), the controller 182 may maintain in its memory a history of recent phase shifter settings used to communicate with each such device. Just prior to a transmission timeslot of such a device, the controller may then retrieve the device's settings and initialize the phase shifters 180 accordingly. In embodiments that use frequency hopping, the transceiver may also capture and store data regarding any frequency dependencies in the phase shift settings. This frequency dependency data may be used to adjust or initialize the phase shifters 180 as the transceiver 56 switches from one frequency to another.

The controller 182 may also support a "scan" mode in which the antenna beam is scanned in an attempt to establish connectivity with a base station. This feature may be used, for example, to search for a base station when no connection currently exists, or to evaluate base stations as "roam" or "switch-over" candidates when a connection exists. The process of scanning for a base station involves initially scanning the antenna beam passively (i.e., without transmitting) in an attempt to locate a "good" base station. Once the transceiver 30 locates a good base station, the transceiver may transmit to that base station a request for a connection, as described generally in U.S. Pat. No. 5,944,659.

Conventional circuits and methods for controlling phased antenna arrays may be used to perform the foregoing functions. The lead wires 42 used to provide the antenna elements of the phased array are preferably of the type shown in FIG. 1 (non-coaxial), but may alternatively be coaxial. The process of scanning the antenna beam may be controlled by firmware executed by a microcontroller of the transceiver 30, or may alternatively be controlled in-whole or in-part by application-specific hardware.

In one embodiment, the phased antenna array is implemented in combination with dynamic impedance matching as described above. Specifically, a dynamically-controlled impedance matching circuit 152 (not shown in FIG. 9) is provided in-line with each antenna conductor 44 on the ECG-lead sides of the phase shifters 180.

IX. Conclusion

Although the various inventive features have been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof Thus, the present invention is defined by the following claims.

What is claimed is:

1. A portable transceiver system for remotely monitoring a patient, comprising:

a lead set having a plurality of electrocardiograph (ECG) leads that attach to a patient to sense ECG waveforms; and a portable transceiver device that receives the ECG waveforms from the ECG lead set, and uses antenna conductors within at least some of the plurality of ECG leads to provide an antenna for communicating bi-directionally with a base station by wireless communications to transfer data representing the ECG waveforms to the base station;

wherein the portable transceiver device provides antenna diversity by automatically switching between at least a first antenna formed from a first set of the ECG leads, and a second antenna formed from a second set of the ECG leads that is different from the first set.

2. The portable transceiver system as in claim 1, wherein the first and second antennas are statically defined within the lead set by way of fixed connections between antenna conductors.

3. The portable transceiver system as in claim 1, wherein the portable transceiver device comprises a switch capable of interconnecting antenna conductors of the ECG leads to form antennas, wherein the switch is controlled to provide at least the first and second antennas.

4. The portable transceiver system as in claim 3, wherein the switch is a matrix switch capable of forming substantially all $2^N-1$ possible combinations of ECG leads, wherein N is the number of ECG leads in the lead set.

5. The portable transceiver system as in claim 4, wherein N is at least 4.

6. The portable transceiver system as in claim 1, wherein at least one ECG lead of the lead set comprises a non-coaxial lead wire having a first conductor which is used to provide at least a portion of the first antenna, and a second conductor which carries an ECG waveform signal of the patient.

7. The portable transceiver system as in claim 6, wherein the first and second conductors extend side-by-side from a connector plug that attaches the lead set to the portable transceiver device, substantially to an ECG electrode connector of the lead.

8. The portable transceiver system as in claim 1, wherein the ECG leads are formed with shielded lead wires, and outer shields of the lead wires are used as the antenna conductors to provide the first and second antennas.

9. The portable transceiver system as in claim 8, wherein the shielded lead wires are coaxial wires.

10. The portable transceiver system as in claim 1, wherein the portable transceiver device selects between at least the first and second antennas based at least in-part on whether a data packet has been successfully received using a currently selected antenna.

11. The portable transceiver system as in claim 1, wherein the portable transceiver device selects between at least the first and second antennas based at least in-part on strengths of signals received by the first and second antennas.

12. The portable transceiver system as in claim 1, wherein the portable transceiver device selects between at least the first and second antennas based at least in-part on antenna impedances monitored by the portable transceiver device.

13. The portable transceiver system as in claim 1, wherein the portable transceiver device selects between at least the first and second antennas based at least in-part on feedback received from a base station regarding a quality of signals received from the portable transceiver device.

14. The portable transceiver system as in claim 1, wherein the first and second sets of ECG leads are mutually exclusive.

15. The portable transceiver system as in claim 1, wherein the first set of ECG leads consists of a Left Arm lead, and the second set of ECG leads consists of Left Leg lead and a Right Arm lead.

16. The portable transceiver system as in claim 1, wherein the first set of ECG leads consists of a Right Leg lead and a Left Arm lead, and the second set of ECG leads consists of a Left Leg lead and a Right Arm lead.

17. The portable transceiver system as in claim 1, wherein the first set of ECG leads consists of a Right Leg lead, and the second set of ECG leads consists of a Left Arm lead, a Left Leg lead and a Right Arm lead.

18. The portable transceiver system as in claim 1, wherein the first set of ECG leads consists of a Right Leg lead, and the second set of ECG leads consists of a Left Arm lead, a Chest lead, a Left Leg lead and a Right Arm lead.

19. The portable transceiver system as in claim 1, wherein the first set of ECG leads consists of a Right Leg lead and a Chest lead, and the second set of ECG leads consists of a Left Arm lead, a Left Leg lead and a Right Arm lead.

20. The portable transceiver system as in claim 1, wherein the first set of ECG leads consists of a Right Leg lead, a Left Arm lead and a first Chest lead, and the second set of ECG leads consists of a Left Leg lead, a Right Arm lead and a second Chest lead.

21. The portable transceiver system as in claim 1, wherein the first set of ECG leads consists of a Right Leg lead, and the second set of ECG leads consists of a Left Arm lead, a first Chest lead, a Left Leg lead, a Right Arm lead and a second Chest lead.

22. The portable transceiver system as in claim 1, wherein the portable transceiver device provides redundancy by transmitting a packet using the first antenna and then retransmitting the packet using the second antenna.

23. The portable transceiver system as in claim 1, wherein the lead set includes at least one additional lead for sensing physiologic data other than ECG signals.

24. A lead set for sensing physiologic data of a patient, comprising:
   a connector for attaching the lead set to a transceiver device; and
   a plurality of electrocardiograph (ECG) leads which extend from the connector to sense ECG signals of a patient, each lead having a single ECG conductor for carrying an ECG signal of the patient and a single antenna conductor;
   wherein the connector has first and second antenna contacts for connecting first and second radio frequency (RF) antennas to the transceiver device, the first antenna contact electrically connected to a first subset of the antenna conductors and the second antenna contact electrically connected to a second subset of the antenna conductors, the first and second subsets being mutually exclusive.

25. The lead set as in claim 24, wherein each ECG lead comprises a non-coaxial lead wire in which the ECG conductor and the antenna conductor extend side-by-side.

26. The lead set as in claim 24, wherein each ECG lead comprises a shielded lead wire in which the antenna conductor is arranged as an outer shield that extends around the ECG conductor along at least a portion of the lead wire.

27. The lead set as in claim 26, wherein each shielded lead wire is a coaxial lead wire.

28. The lead set as in claim 24, wherein the first subset consists of the antenna conductor of a Left Arm ECG lead, and the second subset consists of the antenna conductors of a Left Leg ECG lead and a Right Arm ECG lead.

29. The lead set as in claim 24, wherein the first subset consists of the antenna conductors of a Right Leg ECG lead and a Left Arm ECG lead, and the second subset consists of the antenna conductors of a Left Leg ECG lead and a Right Arm ECG lead.

30. The lead set as in claim 24, wherein the first subset consists of the antenna conductor of a Right Leg ECG lead, and the second subset consists of the antenna conductors of a Left Arm ECG lead, a Left Leg ECG lead and a Right Arm ECG lead.

31. The lead set as in claim 24, wherein the first subset consists of the antenna conductor of a Right Leg ECG lead, and the second subset consists of the antenna conductors of a Left Arm ECG lead, a Chest ECG lead, a Left Leg ECG lead and a Right Arm ECG lead.

32. The lead set as in claim 24, wherein the first subset consists of the antenna conductors of a Right Leg ECG lead and a Chest ECG lead, and the second subset consists of the antenna conductors of a Left Arm lead, a Left Leg lead and a Right Arm lead.

33. The lead set as in claim 24, wherein the first subset consists of the antenna conductors of a Right Leg ECG lead, a Left Arm ECG lead and a first Chest ECG lead, and the second subset consists of the antenna conductors of a Left Leg ECG lead, a Right Arm ECG lead and a second Chest ECG lead.

34. The lead set as in claim 24, wherein the first subset consists of the antenna conductor of a Right Leg ECG lead, and the second subset consists of the antenna conductors of a Left Arm ECG lead, a first Chest ECG lead, a Left Leg ECG lead, a Right Arm ECG lead and a second Chest ECG lead.

35. The lead set as in claim 24, wherein at least one of the first and second subsets comprises antenna conductors of multiple ECG leads.

36. The lead set as in claim 24, wherein the connector comprises a third antenna contact electrically connected to a third subset of the antenna conductors to provide a third RF antenna.

37. The lead set as in claim 24, in combination with a transceiver device which uses the first and second RF antennas to provide antenna diversity.

38. A portable telemetry unit for sensing, and conveying by wireless communications, physiologic data of a patient, the portable telemetry unit comprising:
   a lead set having a plurality of leads for sensing physiologic data of the patient, each lead comprising a flexible lead wire, at least some of the lead wires having conductors that serve as antenna elements for providing a radio frequency (RF) telemetry antenna; and
   a portable telemetry device that receives the physiologic data from the lead set, and transmits the physiologic data by wireless, RF communications to a receiving station using the antenna elements within at least some of the plurality of leads;
   wherein the portable telemetry device provides antenna diversity by automatically switching between at least a first antenna formed from at least a first set of the antenna elements, and a second antenna formed from at least a second set of the antenna elements that is different from the first set.

39. The portable telemetry unit as in claim 38, wherein the portable telemetry device comprises a radio frequency transceiver for communicating bi-directionally with the receiving station.

40. The portable telemetry unit as in claim 38, wherein the portable telemetry device is a radio frequency transmitter device that does not receive data by RF communications.

41. The portable telemetry unit as in claim 38, wherein at least some of the plurality of leads are electrocardiograph leads (ECG) leads.

42. The portable telemetry unit as in claim 38, wherein at least some of the plurality of leads are electroencephalogram (EEG) leads.

43. The portable telemetry unit as in claim 38, wherein at least one of the plurality of leads comprises an $SpO_2$ sensor.

44. The portable telemetry unit as in claim 38, wherein at least one of the plurality of leads comprises an oscillometric blood pressure sensor.

45. The portable telemetry unit as in claim 38, wherein at least one of the first and second antennas comprises an addition antenna element that is not part of a lead.

46. The portable telemetry unit as in claim 38, wherein the first and second antennas are statically defined within the lead set by way of fixed connections between the conductors that serve as antenna elements.

47. The portable telemetry unit as in claim 38, wherein the portable telemetry device comprises a switch capable of interconnecting antenna elements within different leads to form antennas, wherein the switch is controlled to provide at least the first and second antennas.

48. The portable telemetry unit as in claim 38, wherein each conductor that serves as an antenna element extends substantially an entire length of a respective lead wire.

49. The portable telemetry unit as in claim 38, wherein at least one of the conductors that serves as an antenna element is an outer shield of a shielded lead wire.

50. The portable telemetry unit as in claim 38, wherein at least one of the lead wires comprises a first conductor which extends alongside a second conductor in non-coaxial relationship, wherein the first conductor carries physiologic data to the portable telemetry device and the second conductor serves as an antenna element.

51. A method of communicating physiologic data of a patient to a remote location by wireless communications, comprising:
    (a) sensing physiologic data of the patient using a plurality of leads that attach to the patient, wherein at least some of the leads comprise respective antenna conductors;
    (b) selecting between at least a first antenna and a second antenna, wherein the first antenna comprises at least one antenna conductor not included in the second antenna, and the second antenna includes at least one antenna conductor not included in the first antenna;
    (c) transmitting the physiologic data using the antenna selected in (b); and
    (d) repeating (b) and (c) such that both the first antenna and the second antenna are used to transmit the patient's physiologic data.

52. The method as in claim 51, wherein selecting between at least a first antenna and a second antenna comprises selecting between antennas that are statically defined by way of fixed electrical connections.

53. The method as in claim 51, wherein selecting between at least a first antenna and a second antenna comprises using a switch to interconnect antenna conductors of multiple leads to form a multiple-lead antenna.

54. The method as in claim 51, wherein selecting between at least a first antenna and a second antenna comprises selecting an antenna based at least in-part upon strengths of signals received by the first and second antennas.

55. The method as in claim 51, wherein selecting between at least a first antenna and a second antenna comprises selecting an antenna based at least in-part upon current impedance measurements of the first and second antennas.

56. The method as in claim 51, wherein the method comprises transmitting a packet of physiologic data using the first antenna and then the second antenna to provide redundant transmissions.

57. The method as in claim 51, wherein the physiologic data comprises electrocardiograph waveforms.

58. The method as in claim 51, wherein the physiologic data comprises at least one of the following: blood pressure data sensed by an oscillometric blood pressure sensor; $SpO_2$ data; electroencephalogram (EEG) data.

* * * * *